United States Patent [19]

Horenstein

[11] Patent Number: 5,455,507
[45] Date of Patent: Oct. 3, 1995

[54] METHOD AND APPARATUS FOR DETECTING LEAKS IN ELECTRICALLY-INSULATIVE PROTECTIVE ARTICLES SUCH AS CONDOMS, SURGICAL GLOVES AND THE LIKE USING GASEOUS ELECTROSTATIC IONS

[75] Inventor: Mark Horenstein, Newton, Mass.

[73] Assignee: Trustees of Boston University, Boston, Mass.

[21] Appl. No.: 933,645

[22] Filed: Aug. 24, 1992

[51] Int. Cl.⁶ .................................................. G01R 31/12
[52] U.S. Cl. ............................................. 324/557; 324/559
[58] Field of Search ................................. 324/557, 558, 324/559, 551, 554

[56] References Cited

U.S. PATENT DOCUMENTS 2,609,094  9/1952  Fry ............................................ 324/558
4,891,597  1/1990  Asars ......................................... 324/557
5,204,632  4/1993  Leach ........................................ 324/557

*Primary Examiner*—Walter E. Snow
*Attorney, Agent, or Firm*—Kriegsman & Kriegsman

[57] ABSTRACT

A method and apparatus are described for detecting defects in a condom, protective glove or other similar product during manufacture. The product to be tested is situated on an electrically conductive mandrel, the shape of the mandrel corresponding to the shape of the product. Ions of air are generated and driven toward the mandrel. The flow of ions of air into the mandrel through any holes or tears in the product is detected by measuring the constant current flow through the mandrel. Thickness variations in the product are detected by measuring the duration of the transient current flow through the mandrel.

1 Claim, 2 Drawing Sheets

5,455,507

METHOD AND APPARATUS FOR DETECTING LEAKS IN ELECTRICALLY-INSULATIVE PROTECTIVE ARTICLES SUCH AS CONDOMS, SURGICAL GLOVES AND THE LIKE USING GASEOUS ELECTROSTATIC IONS

BACKGROUND OF THE INVENTION

The present invention relates to a method and apparatus for detecting defects in condoms, protective gloves and other similar products and more particularly to a method and apparatus for detecting defects in condoms, protective gloves and other similar products using electrostatic ions of a gas.

Condoms and protective gloves, i.e. gloves used for health care purposes, are very often made of latex or vinyl and fabricated on a mandrel. In the manufacturing of such products, a mandrel of the desired shape is dipped into a container having a supply of the material from which the product is to be made, the material being in liquid form. After a predetermined period of time, the mandrel is withdrawn from the container. The product which has been formed on the mandrel is then allowed to dry and be cured.

As can be appreciated, it is extremely important that protective gloves, condoms and other similar products be free of defects; that is, have no holes or tears or any areas of weakness which may produce holes or tears during use.

One way that has been employed in the past to test for holes or tears in condoms during the manufacture thereof has been to place a condom to be tested on a metallic mandrel (or use a metallic mandrel to fabricate the condom), place the metallic mandrel with the condom on it into a metal container filled with a liquid electrolyte, establish a voltage difference between the container and the metallic mandrel and then measure the resulting current flow, if any, in the mandrel. If there are any holes or tears in the condom, current will flow through the container and the mandrel, the current being carried between the container and the mandrel through the ions in the liquid electrolyte. On the other hand, if there are no holes or tears in the condom there will be no current flow since the condom will serve as an electrical insulator between the mandrel and the electrolyte. One disadvantage with this testing arrangement is that the condom becomes wet when it is immersed In the liquid electrolyte and as a result has to be dried before it can be packaged for later use. This additional step of drying the condom is time consuming and costly. Another disadvantage with this testing arrangement is that because of the skin surface tension and viscosity of the liquid electrolyte, holes or tears in the condom will only be detected that are above a certain minimum size. If the hole or tear is below that certain minimum size, the liquid will not pass through and come into contact with the mandrel. Consequently, there will be no current flow through the mandrel. Still another disadvantage with this testing procedure Is that it is not used to test each and every condom that is being produced, but, rather, only selected condoms. As is apparent, this arrangement is not very satisfactory since it is important that every condom that is going to be used be tested and not merely selected condoms. Also, this testing procedure has only been used in detecting holes or tears and not for monitoring thickness.

Another testing procedure that has been employed in the past to detect defects in condoms during the manufacture thereof has been to remove a condom from the production line, fill it with a liquid and then squeeze it until it breaks. As can be appreciated this procedure is only a quality control type of test rather than a test for each and every condom being manufactured. Also, it is a destructive type of test in that the condom so tested cannot be subsequently put into use.

Accordingly, it is an object of this invention to provide a new and improved method and apparatus for detecting defects In condoms, protective gloves and other similar products.

It is another object of this invention to provide a method and apparatus for detecting defects in condoms, protective gloves and other similar products which does not involve the use of any liquids.

It is still another object of this invention to provide a method and apparatus for detecting defects In condoms, protective gloves and other similar products which can be performed on each product while it is on the production line.

It is yet still another object of this invention to provide a method and apparatus for detecting defects In condoms, protective gloves and other similar products in a very short period of time.

It is a further object of this invention to provide a method and apparatus for detecting defects in condoms, protective gloves and other similar products without moving it to a separate testing station.

It is another object of this invention to provide a method and apparatus for detecting defects in condoms, protective gloves and other similar products without having to touch the product.

It is still another object of this invention to provide a method and apparatus for detecting holes and/or tears in condoms, protective gloves and other similar products.

It is yet still another object of this invention to provide a method and apparatus for monitoring the thickness of condoms, protective gloves and other similar products during the manufacture thereof.

It is a further object of this invention to provide a method for detecting defects in condoms, protective gloves and other similar products which is non-destructive.

SUMMARY OF THE INVENTION

A method of detecting defects in a condom, protective glove or other similar product according to this invention comprises providing an electrically conductive mandrel, the shape of the electrically conductive mandrel corresponding to the shape of the product, situating the product on said electrically conductive mandrel, generating ions of a gas and causing said ions to be driven toward said mandrel, and then measuring the current flow through the electrically conductive mandrel, the current flow through the electrically conductive mandrel depending on the condition of the product.

Apparatus for detecting defects in a condom, protective glove or other similar product according to this invention comprises an electrically conductive mandrel, the shape of the electrically conductive mandrel corresponding to the shape of the product, means for generating ions of a gas and driving the said ions toward said electrically conductive mandrel, and then means for measuring the current flow through the electrically conductive mandrel, said current flow depending on the condition of said protective product.

If there is a hole or tear in the product gaseous ions will pass through to the mandrel, producing a current flow through the mandrel which can be detected. In addition, by measuring the duration of the transient current flow through the mandrel (i.e. The capacitive signal passing through product) a signal can be obtained which is related to the thickness of the product.

Various features and advantages will appear from the description to follow. In the description, reference is made to the accompanying drawings which forms a part thereof, and which is shown by way of illustration, specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is therefore, not to be taken in a limiting sense, and the scope of the present invention is best defined by the appended claims.

BRIEF DESCRIPTION OF THE DRAWINGS

In the drawings wherein like reference numerals represent like parts.

DETAILED DESCRIPTION OF PREFERRED EMBODIMENTS

Figure 1:
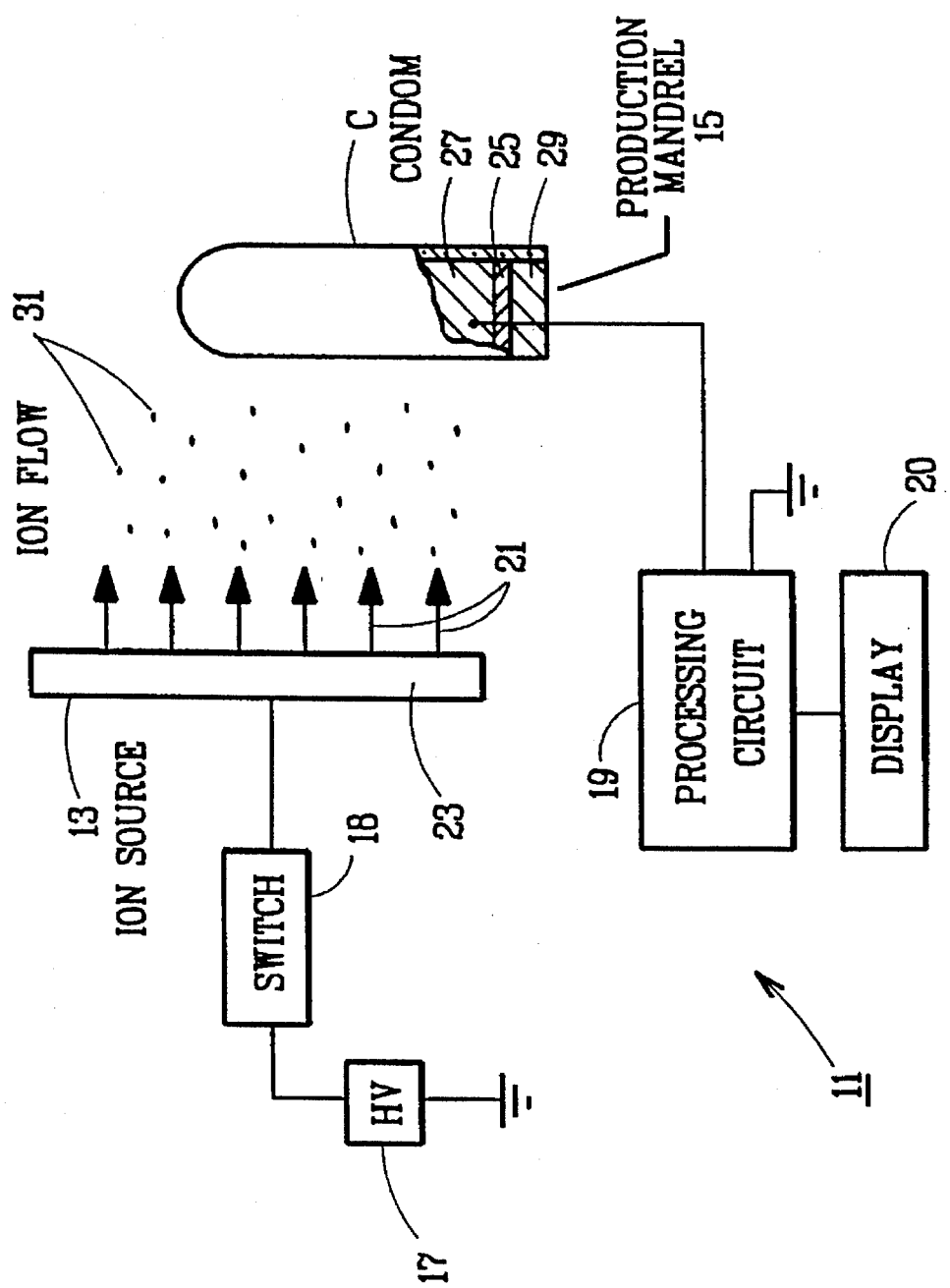
FIG. 1 is a simplified schematic diagram of an apparatus constructed according to one embodiment of this invention, for detecting defects in a condom, the condom being shown broken away in part.

Referring now to the drawings, there is shown in FIG. 1 a schematic diagram of an apparatus constructed according to the teachings of this invention for detecting defects in a product of the type described above, the apparatus being identified by reference numeral 11. For illustrative purposes only, the product shown being tested is a condom identified by reference letter C. Condom C is made of latex, vinyl or other electrically insulative material.

Apparatus 11 includes a corona type ion source 13 for generating gaseous ions, a mandrel 15 for holding condom C, an AC high voltage source 17 for driving ion source 13 to produce ions and to drive the ions generated thereby toward mandrel 15, an on-off switch 18 for coupling source 17 to ion source 13 and a detection and processing circuit 19 for detecting current flow through mandrel 15 and processing the current signals so detected and a display 20 for displaying results.

Ion source 13 and mandrel 15 are surrounded by air. Instead of air, ion source 13 and mandrel 15 may be surrounded by any other gaseous medium, preferably, one that is inert.

Ion source 13 may be any known type of ionizer which will ionize a gas in proximity to it when subjected to voltage above a certain threshold value. Ion source 13 may be, for example, a set of needle points 21 on a base 23, needle points 21 and base 23 both being made of electrically conductive material.

High voltage source 17 produces a continuous AC voltage and may be, for example, a voltage source which produces a voltage of about 5000 volts AC. Since voltage source 17 is an AC type voltage source, the ions produced are bipolar.

Mandrel 15 is shaped to support condom C and may be the same mandrel that is used to fabricate condom C. If the product being tested is not a condom, i.e. a glove or other type of product which is formed on a mandrel, then the mandrel will be shaped accordingly to hold (or fabricate) that other type of product. Mandrel 15 is made of a glass substrate 25 which is coated on its sidewall with a layer of electrically conductive material, such as copper. The layer is deposited on substrate 25 so that it forms a top portion 27 and a bottom portion 29, bottom portion 29 being spaced from top portion 27. As can be seen, top portion 27 is sized so that it is just about entirely covered by condom C while bottom portion 29 is not covered at all by condom C.

Mandrel 15 is spaced a few centimeters (i.e. about 3 to 5 centimeters) from ion source 13.

Circuit 19 is electrically coupled to top portion 27 of the layer of conductive material and includes current flow detector and processing circuitry.

In the operation of apparatus 11, when on-off switch 18 is turned on ions of air 31 will be generated by ion source 13 and driven toward mandrel 15. Because of electrostatic attraction, ions 31 will curve around mandrel 15. Initially, there will be a small transient current flowing through mandrel 15. The reason for this is as follows. If the ions and the mandrel are considered equivalent to the plates of a capacitor, the transient current will flow for the time it takes to change the capacitor. This transient current signal will decay to zero after a very small period of time i.e. after the capacitor is charged up. The duration of this transient current is related to the thickness of the material of condom C i.e. the thicker the material the longer the time period. The time period of the transient current is measured and processed by circuit 19 and then displayed on display 20. In this manner, thickness variations from one condom to the next on the production line can be detected.

In addition to the transient current signal, if there are any holes or tears in condom C, ions will pass through to mandrel 15 producing as a result a continuous AC current flow through mandrel 15. This continuous AC current flow is detected and processed by circuit 19 and then displayed on display 20.

If there are no holes or tears in condom C, there will not be any continuous current flow through mandrel 15, only the transient current flow.

Instead of being made of glass coated with a conductive coating, mandrel 15 could be made of a top piece of conductive material, a bottom piece of conductive material and a spacer of insulative material separating the top piece and the bottom piece from each other. The conductive material could be, for example, stainless steel.

Figure 2:
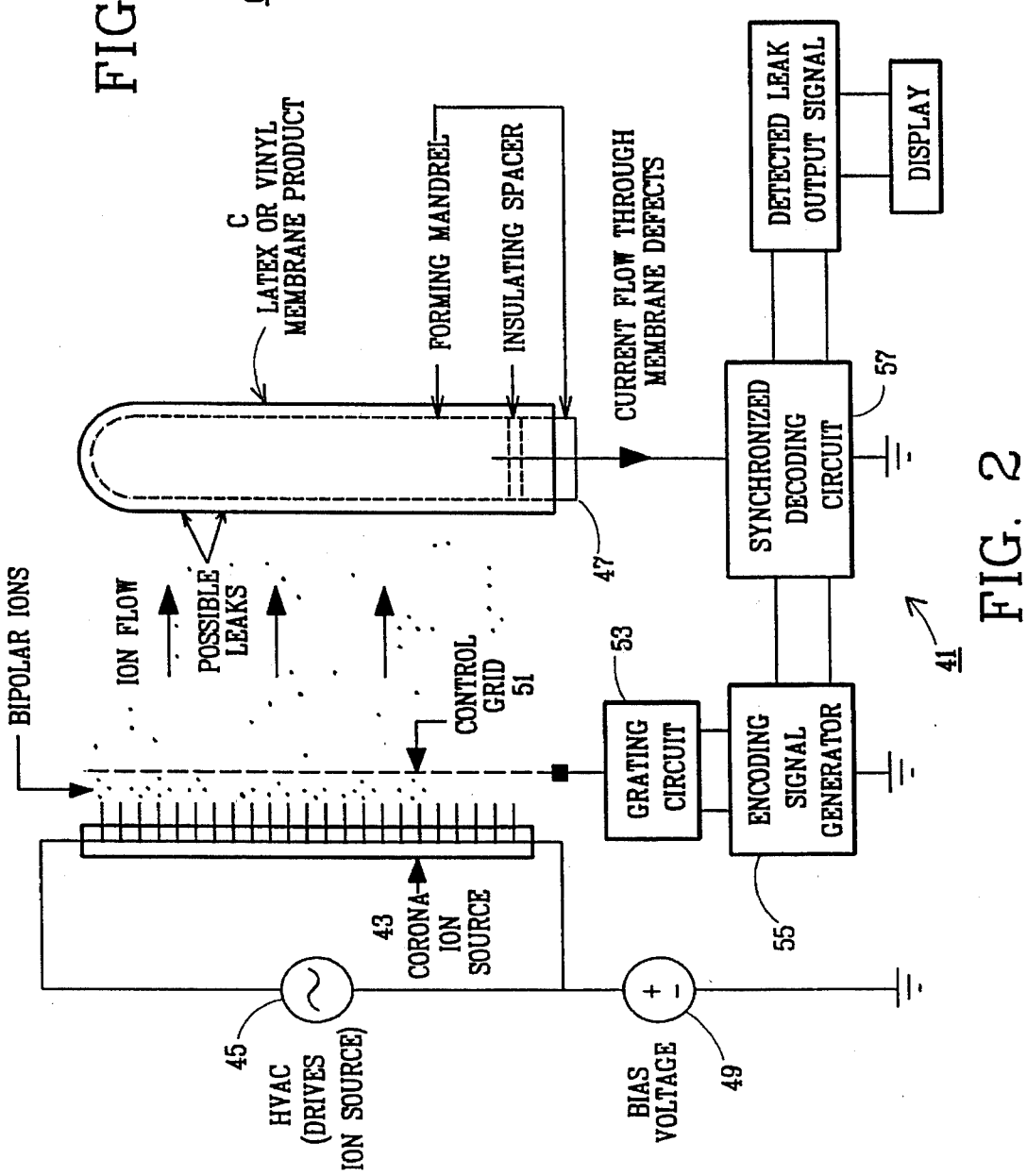
FIG. 2 is a simplified schematic diagram of an apparatus constructed according to another embodiment of this invention, for detecting defects in a condom, the condom being shown broken away in part.

Referring now to FIG. 2 there is shown a simplified schematic of another embodiment of the invention, the apparatus being identified by reference numeral 41.

Apparatus 41 includes a corona type ion source 43 for generating ions of the gaseous medium surrounding it, a high voltage source 45 for driving ion source 43 to produce ions, a mandrel 47 for holding a condom C to be tested, a bias voltage source 49 for driving the ions produced by ion source 43 toward mandrel 47, a control grid 51 for controlling the flow of ions toward mandrel 47, a gating circuit 53 for controlling control grid 51, an encoding signal generator 55 for encoding the output signal sent out from gating circuit 53, a decoding circuit 57 for decoding the signal received from mandrel 47, a detector 59 for detecting and processing current signals received from decoding circuit 57 and a display 61 coupled to detector 59.

Ion source 43 is the same as ion source 13. High voltage source 45 is an AC type voltage source similar to voltage source 17. Since voltage source 45 is an AC type voltage source, the ions produced thereby will be bipolar. Mandrel 47 is identical to mandrel 15. Voltage source 49 produces a DC voltage and is used to drive the ions generated by ion source 43 toward mandrel 47. Voltage source 49 may be, for example 30 volts DC. Control grid 51 is used to gate the flow of ions from ion source 43 toward mandrel 47 in gating circuit 53 sends out a signal which controls control grid 51. The signal outputted by gating circuit 53 is a stepped, enclosed signal, achieved by encolding signal generator 55.

Apparatus 41 operates in a manner similar to apparatus 11. Bipolar ions generated when ion source 43 is driven by source 45 are driven by bias voltage 49 toward mandrel 47. Flow of ions from source 45 is controlled by control grid 51. Transient current signals produced in mandrel 47 are related to the thickness of condom C and if there are any holes or tears in condom C there will be a continuous output current signal in addition to the transient current signal 59. Encoding of the gating circuit signal is used to reduce noise. Detector 59 is similar to detecting and processing circuit 19.

Instead of a single ion source, ions could be generated by a plurality of ion sources circumferentially spaced around the mandrel on which the product is mounted.

Also the ion source could be mounted for movement around the mandrel or the mandrel mounted for rotation relative to the ion source.

Figure 3:
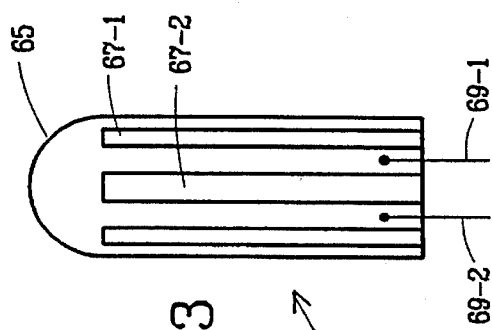
FIG. 3 is a side view of a modified version of the mandrel shown in FIG. 1.

In FIG. 3 there is shown another mandrel which may be used with this invention. The mandrel being identified by reference numeral 63. Mandrel 63 is made of a glass substrate 65 on which is deposited a plurality of longitudinal spaced apart conductive strips 67-1, 67-2, etc., each strip being connected to a separate electrical wire 69-1, 69-2, etc. Mandrel 63 may be used to monitor the thickness at different areas on the condom by measuring the transient current at each strip when the condom while on the mandrel is exposed to gaseous ions from a suitable source. As can be appreciated, however, this mandrel will not detect holes or tears for locations on the condom in front of the mandrel at places which are not covered with the conductive materials; i.e. The areas between the conductive strips.

If desired, the high voltage source used in both embodiments above to produce the ions could be DC rather than AC. However, if a DC high voltage source is used the ions produced will not be bipolar and will have a tendency to remain on the product when the drive voltage is turned off.

The embodiments of the present invention are intended to be merely exemplay and those skilled in the art shall be able to make numerous variations and modifications to it without departing from the spirit of the present invention. All such variations and modifications are intended to be within the scope of the present invention as defined in the appended claims.

What is claimed is:

1. A method of testing, during manufacture, an electrically-insulative protective article for leaks, the method comprising the steps of:
   a. providing an electrically conductive mandrel, the shape of said electrically conductive mandrel corresponding to the desired shape of the electrically-insulative protective article to be formed thereon;
   b. forming the electrically-insulative protective article on said electrically conductive mandrel;
   c. generating ions of a gas and causing said ions to be driven towards said electrically conductive mandrel with the electrically-insulative protective article formed thereon; and
   d. measuring the continuous current flow through the electrically conductive mandrel, said continuous current flow being indicative of the existence of leaks in the electrically-insulative protective article.

* * * * *